(12) United States Patent
Huang et al.

(10) Patent No.: US 11,971,635 B2
(45) Date of Patent: Apr. 30, 2024

(54) U-SHAPED UNIT AND LIQUID CRYSTAL ELEMENT WITH U-SHAPED COPLANAR ELECTRODE UNITS

(71) Applicant: Tunghai University, Taichung (TW)

(72) Inventors: Chia-Yi Huang, Taichung (TW); Wei-Fan Chiang, Taichung (TW); Yi-Hong Shih, Taichung (TW)

(73) Assignee: TUNGHAI UNIVERSITY, Taichung (TW)

( * ) Notice: Subject to any disclaimer, the term of this patent is extended or adjusted under 35 U.S.C. 154(b) by 0 days.

(21) Appl. No.: 18/154,952

(22) Filed: Jan. 16, 2023

(65) Prior Publication Data

US 2023/0152637 A1 May 18, 2023

Related U.S. Application Data

(63) Continuation-in-part of application No. 17/322,290, filed on May 17, 2021, now abandoned.

(51) Int. Cl.
*G02F 1/1343* (2006.01)
*G01N 33/49* (2006.01)
*G02F 1/137* (2006.01)

(52) U.S. Cl.
CPC .. *G02F 1/134363* (2013.01); *G02F 1/134372* (2021.01); *G02F 1/134381* (2021.01); *G02F 1/13439* (2013.01); *G01N 33/49* (2013.01); *G02F 1/13706* (2021.01); *G02F 1/13793* (2021.01)

(58) Field of Classification Search
None
See application file for complete search history.

(56) References Cited

U.S. PATENT DOCUMENTS 10,025,147 B2 * 7/2018 Ma ............... G02F 1/134363
2010/0302492 A1 * 12/2010 Kubota ........ G02F 1/134363
349/138

* cited by examiner

*Primary Examiner* — Dung T Nguyen
(74) *Attorney, Agent, or Firm* — Guice Patents PLLC

(57) ABSTRACT

A U-shaped unit and a liquid crystal element with U-shaped coplanar electrode units provided by the invention are capable of increasing a horizontal electric field intensity in a power supply state, so that when the invention is applied to be used as a liquid crystal driving element, a required horizontal electric field intensity can be achieved with a lower driving voltage to reduce a required driving power when the liquid crystal element is used as a display screen, thereby achieving an effect of power saving.

11 Claims, 13 Drawing Sheets

U-SHAPED UNIT AND LIQUID CRYSTAL ELEMENT WITH U-SHAPED COPLANAR ELECTRODE UNITS

CROSS REFERENCE TO OTHER APPLICATIONS

This application is a continuation-in-part of U.S. application Ser. No. 17/322,290 filed May 17, 2021, the disclosures of which are hereby incorporated by reference as if fully restated herein.

BACKGROUND OF THE INVENTION

Field of Invention

The invention is related to electric field technology, and more particularly to a U-shaped coplanar electrode unit capable of increasing a horizontal electric field intensity.

Related Art

The technical means of using electric field to control the alignment of liquid crystal molecules and change the refraction angle of backlight in order to achieve color conversion is a well-known principle of liquid crystal display devices. Different liquid crystal display technologies developed on this basis are still being disclosed in recent years. Disclosed alignment technologies for forming an appropriate electric field between the two baseplates filled with liquid crystal include multi-domain vertical alignment (MVA) in which electrodes are provided on both sides of the liquid crystal layer to form an electric field between the two electrodes after electric power is supplied; in-plane-switching (IPS) in which an electrode is disposed on one side of the liquid crystal layer to form an electric field above the electrode after electric power is supplied; as well as other alignment technologies developed based on the above alignment technologies, for example, A-MVA, FSS, etc.

With the development of technologies, the control of liquid crystals is no longer just a mere alignment to achieve the object of changing colors. In the increasingly sophisticated technological development, current display technologies are developed in a direction towards obtaining effects of wider viewing angle, shorter response time, and better color contrast.

However, while further improving the liquid crystal display technology, the conventional technology has not been able to effectively reduce the driving voltage of liquid crystal alignment, especially in the technical field of using IPS. Since the pixel electrode and the common electrode usually extend opposite to each other on the same horizontal plane, as shown in FIG. 1. While an electric field of IPS, as shown in FIG. 2, a parabolic electric field is formed above a pixel electrode 1 and common electrodes 2, under this form of electric field, the transverse component formed in the horizontal direction is limited, and it is difficult to form electric field in the vertical direction positions of the electrodes 1, 2, and therefore the intensity of the horizontal electric field formed is limited. In order to increase the intensity of the horizontal electric field, the conventional technology can only achieve it by increasing the driving voltage. However, it causes a drawback of excessively high driving voltage. As a result, in order to drive the liquid crystal for display, it is necessary to consume more electric power energy, which makes the screen display element the most power-consuming component in a smart phone.

SUMMARY OF THE INVENTION

Therefore, a main object of the invention is to provide a U-shaped unit capable of increasing an aspect ratio of side portions with free ends on two sides of the U-shape in order to improve effects produced by the U-shaped unit in industrial applications by the side portions with high aspect ratio, such as increasing a horizontal electric field intensity, increasing a heat dissipation surface area, used as unit integration of an optical element or a unit of a biosensing element, wherein, in the effect of increasing the horizontal electric field intensity, the U-shaped unit can be used as a constituent unit of an electrode element to be served as a U-shaped coplanar electrode unit, thereby increasing the horizontal electric field intensity under electric power supply state, so that when the U-shaped unit is applied to be used as a liquid crystal driving element, a required horizontal electric field intensity can be achieved with a lower driving voltage to reduce a required driving power when the liquid crystal element is used as a display screen, thereby achieving an effect of power saving.

In order to achieve the above object, the U-shaped coplanar electrode unit provided by the invention makes the electrode unit generally U-shaped, and has a base corresponding to a U-shaped closed end position, and two side portions corresponding to two side positions of the U-shape, and a ratio between a width and a height of each of the side portions is between 1:20 and 1:2, so that two side planes of each of the side portions parallel to the height direction can be used as electrode planes.

In the U-shaped coplanar electrode unit, the electrode unit can be miniaturized to be used as an electrode of a liquid crystal display element, when the U-shaped coplanar electrode unit is used as the electrode of the liquid crystal display element, in addition to disposing a plurality of electrode units on a same side of a liquid crystal layer, the electrode units can also be disposed on different sides of the liquid crystal layer.

Wherein, when the electrode units are disposed on different sides of the liquid crystal layer, U-shaped openings of the electrode units on the different sides are facing each other in a staggered manner, so that a single side portion of each of the electrode units on one of the sides and a single side portion of each of the electrode units on the other side are inserted into the U-shaped opening of each other, and the electrode units on the different sides are arranged in a staggered manner.

Another object of the invention is to provide a unit structure with a high aspect ratio, which has a base and side portions extending from two sides of the base in a same direction outwardly along a predetermined angle direction, and a ratio between a width and a height of each of the side portions is between 1:2 and 1:20. A high and narrow shape of each of the side portions is provided as a component in the field of microelectronic technology, for example, as the aforementioned electrode unit, as a heat dissipation unit of a heat dissipation element or a unit of a biosensing element.

Further, another object of the invention is to provide a unit structure, which has a U-shaped unit formed on a baseplate, and the base is arranged on a first side plate surface of the baseplate, extending the width along a virtual first axis direction parallel to the plane of the first side plate surface. Each of the side portions is from the two ends of the base in the first axis direction, respectively along a second axis direction separated from the first axis direction by a predetermined angle and not on the same plane as the first axis, respectively extending outward away from the baseplate, and jointly form a U-shaped section with the base, so that the U-shaped unit forms a three-dimensional structure on the baseplate.

BRIEF DESCRIPTION OF THE DRAWINGS

FIG. 17 is a heat dissipation efficiency diagram of a traditional metal plate and a metal plate with U-shaped coplanar electrode unit disposed on;

DETAILED DESCRIPTION OF THE INVENTION

In order to enable the examiner to further understand the objects, features, and achieved efficacies of the invention, three preferred embodiments are described below for detailed explanation in conjunction with the drawings.

Figure 1:
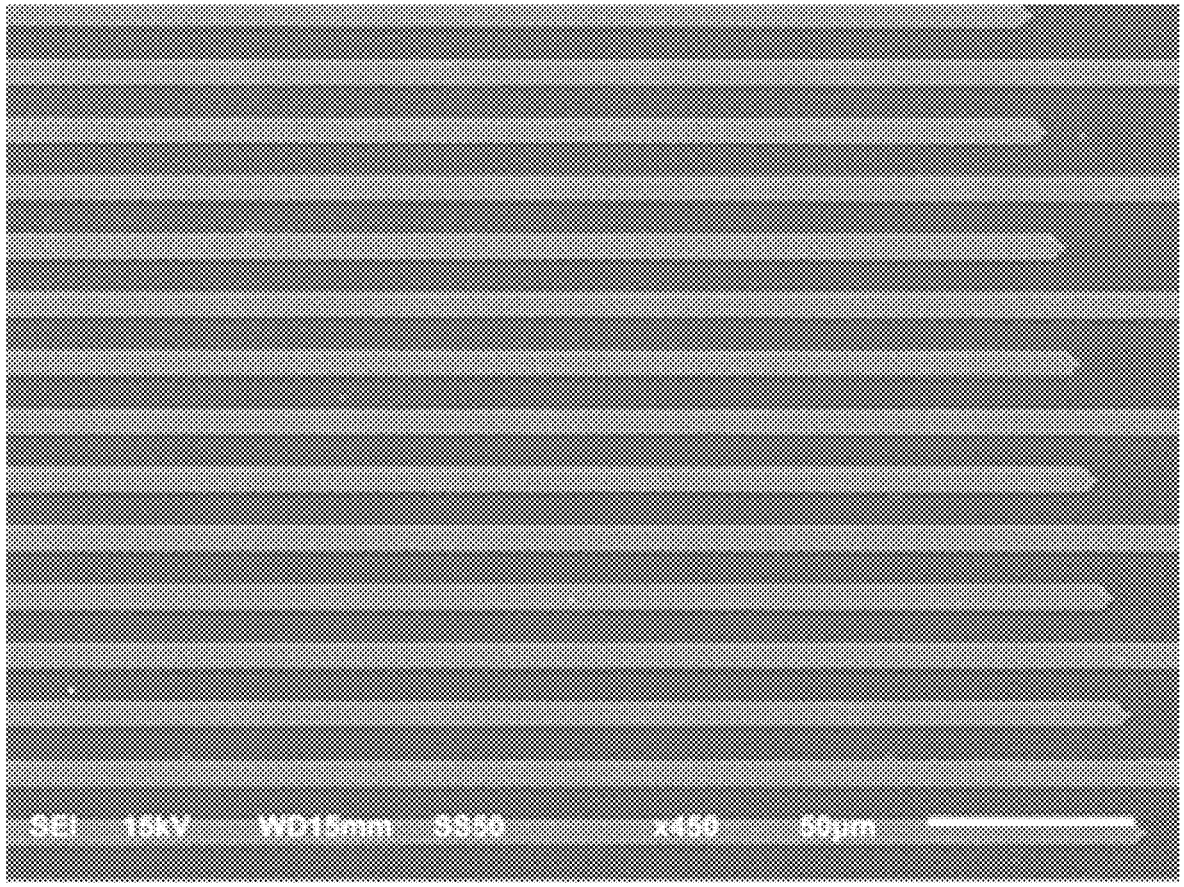
FIG. 1 is a schematic diagram of a conventional electrode taken by a scanning electron microscope (SEM)
Figure 2:
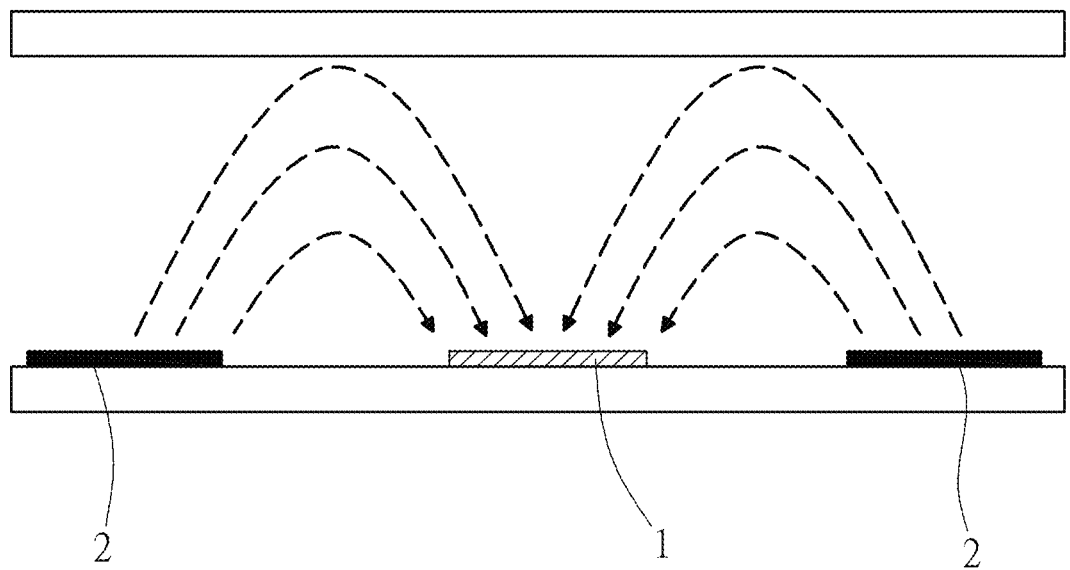
FIG. 2 is a plan view of the conventional in-plane-switching (IPS) technology.
Figure 3:
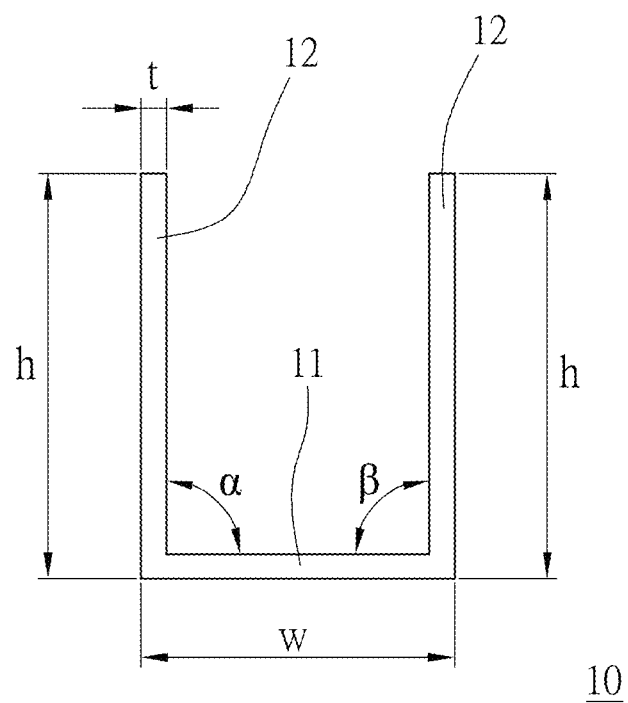
FIG. 3 is a plan view of a first preferred embodiment of the invention.

First of all, please refer to FIG. 3. A U-shaped unit 10 provided in a first preferred embodiment of the invention comprises a strip-shaped base 11 and two strip-shaped side portions 12 respectively disposed on two sides of the base 11.

In terms of shape, the U-shaped unit 10 is in a U-shape with the base 11 as a bottom and each of the side portions 12 as a wall, wherein although included angles α, β between each of the side portions 12 and the base 11 are shown as an included angle of 90 degrees in the Figure, the included angles are not limited thereto, an angular degree of the included angle is any value between 45 degrees and 135 degrees, also, it is not necessary to make the included angle between each of the side portions 12 and the base 11 the same. It should be emphasized here that the base 11 is used as a basis, and a height of each of the side portions 12 being formed can be increased, so that a ratio between a height and a width of each of the side portions 12 can be expanded to 20:1, thereby increasing an action range of each of the side portions 12, so that the U-shaped unit 10 is capable of producing efficacy better than the conventional technologies.

In terms of dimension, a width w of the base 11 between two ends of its strip-shape is between 3 nm and 20 µm. A height h is measured from one end of each of the side portions 12 connected with the base 11 to a free end of each of the side portions 12, a width t is a dimension of each of the side portions 12 parallel to a direction of the width w, and a ratio between the width t and the height h is preferably between 1:20 and 1:2. Specifically, the height h of each of the side portions 12 is between 3 nm and 20 µm, and the width t of each of the side portions 12 is between 3 nm and 2 µm.

In terms of material, constituent elements of the U-shaped unit 10 can be made of a same material or different materials, depending on requirements of an actual product, transparent conductive material, metal material, dielectric material or semiconductor material can be used to make the electrode unit 10. The transparent conductive material can be, for example, indium tin oxide, indium zinc oxide, indium gallium zinc oxide, indium tin zinc oxide, aluminum tin oxide, aluminum zinc oxide, cadmium tin oxide or cadmium zinc oxide. The metal material can be gold, silver, copper, iron, aluminum, platinum, titanium, indium, molybdenum, tin, manganese or zinc. The dielectric material can be titanium dioxide, silicon dioxide, silicon nitride, silicon oxide, nitrides of silicon, calcium titanate, magnesium titanate, barium titanate or composite oxides. The semiconductor material can be aluminum gallium nitride, aluminum nitride (indium) gallium, gallium arsenide, gallium phosphide or indium antimonide. Selection of materials is general knowledge to those having ordinary skill in the art to which the invention pertains, selection can be made according to the ordinary skill at the time of application of the invention, and according to requirements of a product to which the U-shaped unit 10 is applied, the materials are only provided as examples by the invention, and types of the materials should not be used as limiting conditions to limit the scope of the claims of the invention.

Figure 4:
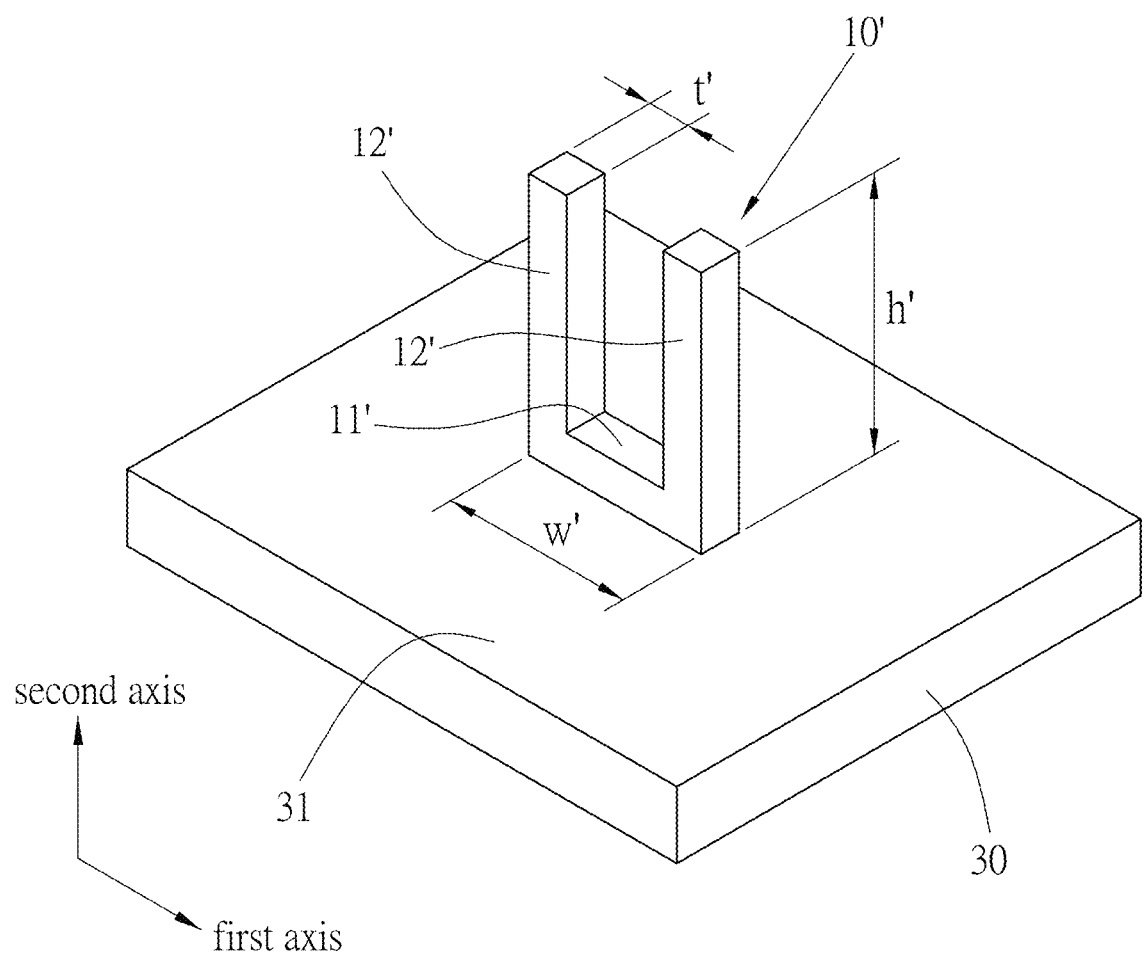
FIG. 4 is a perspective view of a second preferred embodiment of the invention.

Please continue referring to FIG. 4, in the third preferred embodiments of the present invention, the differences from the first preferred embodiment are that the U-shaped unit (10') is molded on a baseplate (30), and the base (11') is arranged on a first side plate surface (31) of the baseplate (30), extending the width (w') along a virtual first axis direction parallel to the plane of the first side plate surface (31). Each of the side portions (12') is from the two ends of the base in the first axis direction, respectively along a second axis direction separated from the first axis direction by a predetermined angle and not on the same plane as the first axis, respectively extending outward away from the baseplate (30), and jointly form a U-shaped section with the base, so that the U-shaped unit (10') forms a three-dimensional structure on the baseplate (30). In this example, the included angle between the first axis and the second axis is 90 degrees, and in other possible implementations, the included angle is any value between 45 degrees and 135 degrees. In addition, the ratio of the individual width (t') of each side portions (12') in the direction of the first axis to the individual height (h') in the direction of the second axis is between 1:20 and 1:2.

In addition, in this example, the first axis is the X axis or the Y axis, and the second axis is the Z axis.

Figure 5:
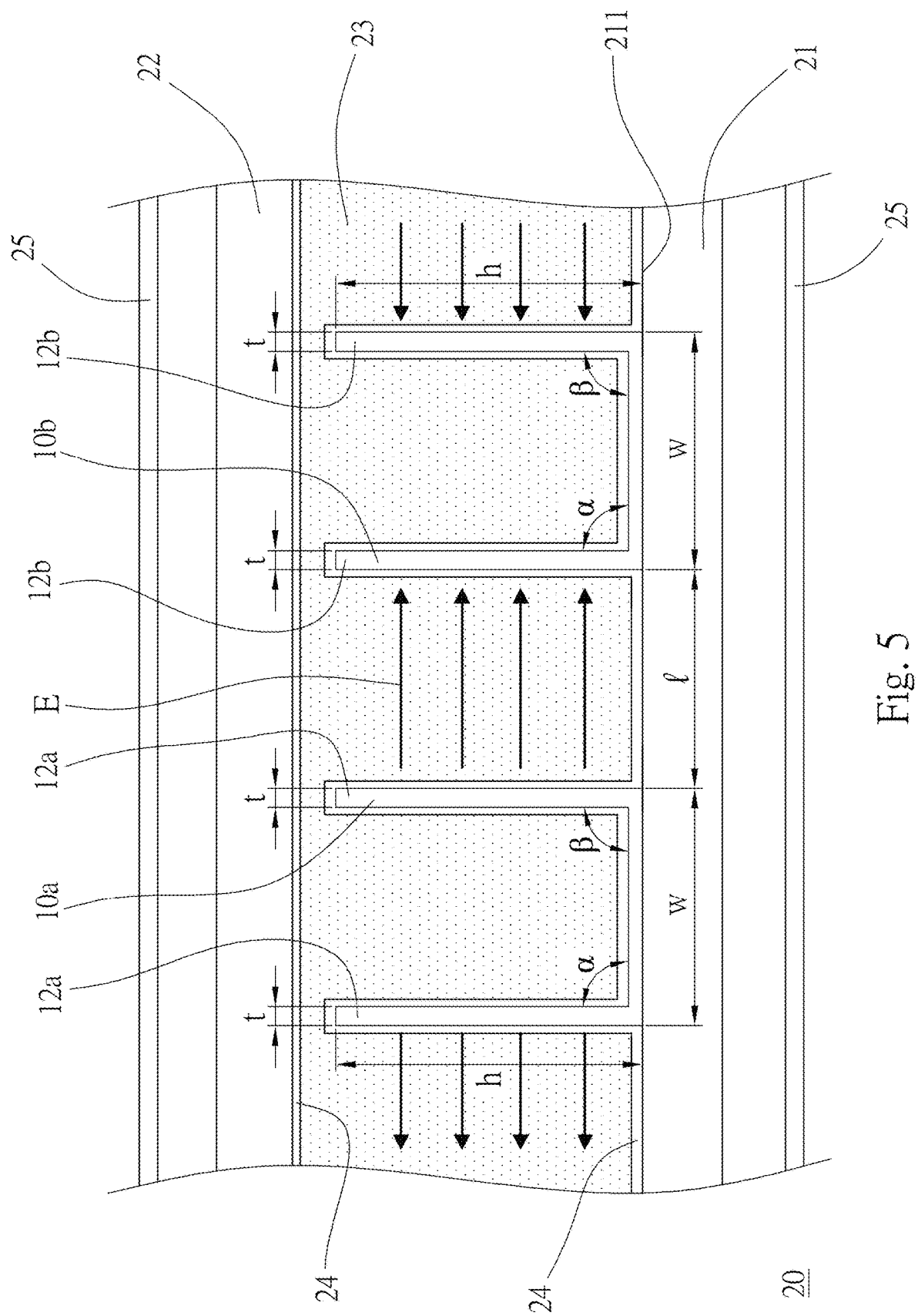
FIG. 5 is a partial plan view of a third preferred embodiment of the invention.

Please continue referring to FIG. 5. A third preferred embodiment of the invention is a specific application example of the U-shaped unit 10 disclosed in the first preferred embodiment as the U-shaped coplanar electrode unit (10), and the electrode units 10 are respectively used as common electrodes 10a and pixel electrodes 10b of a liquid crystal element 20.

The liquid crystal element 20 mainly comprises a first baseplate 21, a second baseplate 22 separated from the first baseplate 21 with a spacing of 1 μm to 25 μm, and a liquid crystal layer 23 sealed between the first baseplate 21 and the second baseplate 22, wherein the liquid crystal layer 23 is made of positive type liquid crystal material in this embodiment, but it is not limited thereto in specific implementation, the liquid crystal layer 23 can also be negative type liquid crystal, ferroelectric liquid crystal, polymer dispersed liquid crystal, polymer stabilized liquid crystal or blue phase liquid crystal. In addition, the liquid crystal element 20 further comprises alignment films 24 respectively located on two sides of the liquid crystal layer 23, and polarizers 25 respectively located on outer sides of the first baseplate 21 and the second baseplate 22, which are contents of the conventional technologies that will not be described herein.

In this embodiment, each of the electrode units 10 is disposed on a same side of the liquid crystal layer 23, that is, on a side 211 of the first baseplate 21 facing the second baseplate 22 as shown in FIG. 5. According to requirements of alignment technology, a part of each of the electrode units 10 is used as the common electrode 10a, another part of each of the electrode units 10 is used as the pixel electrode 10b, and an interval l spaced between the common electrode 10a and the pixel electrode 10b adjacent to each other is between 3 nm and 20 μm.

Thereby, after voltage is supplied, a horizontal electric field E can be formed between the common electrode 10a and the pixel electrode 10b, and at the same time, the height h of each of side portions 12a, 12b is greater than half of a distance between the first baseplate 21 and the second baseplate 22, so that a range of the horizontal electric field E formed is capable of reaching the entire liquid crystal layer 23; thereby, a lower voltage can be used to obtain a horizontal electric field intensity sufficient to achieve an object of liquid crystal alignment. For example, as shown in FIG. 6, in this embodiment, the height h is fixed to 10 μm, and the width t is fixed to under 0.5 μm, by changing values of the width w and the interval l, a voltage-transmittance graph can be obtained, wherein:

when both the width w and the interval l are 10 μm, driving voltage is 3.51V and transmittance is 0.21;
when both the width w and the interval l are 7 μm, driving voltage is 2.88V and transmittance is 0.21;
when both the width w and the interval l are 4 μm, driving voltage is 2.31V and transmittance is 0.20;
it can be known that when the electrode unit 10 is used as each of the common electrodes 10a and each of the pixel electrode 10b, compared with the conventional in-plane-switching (IPS) often requiring a voltage of 4V-6V to be sufficient to achieve an object of liquid crystal alignment, the invention is indeed capable of reducing driving voltage and reducing power consumption.

Figure 6:
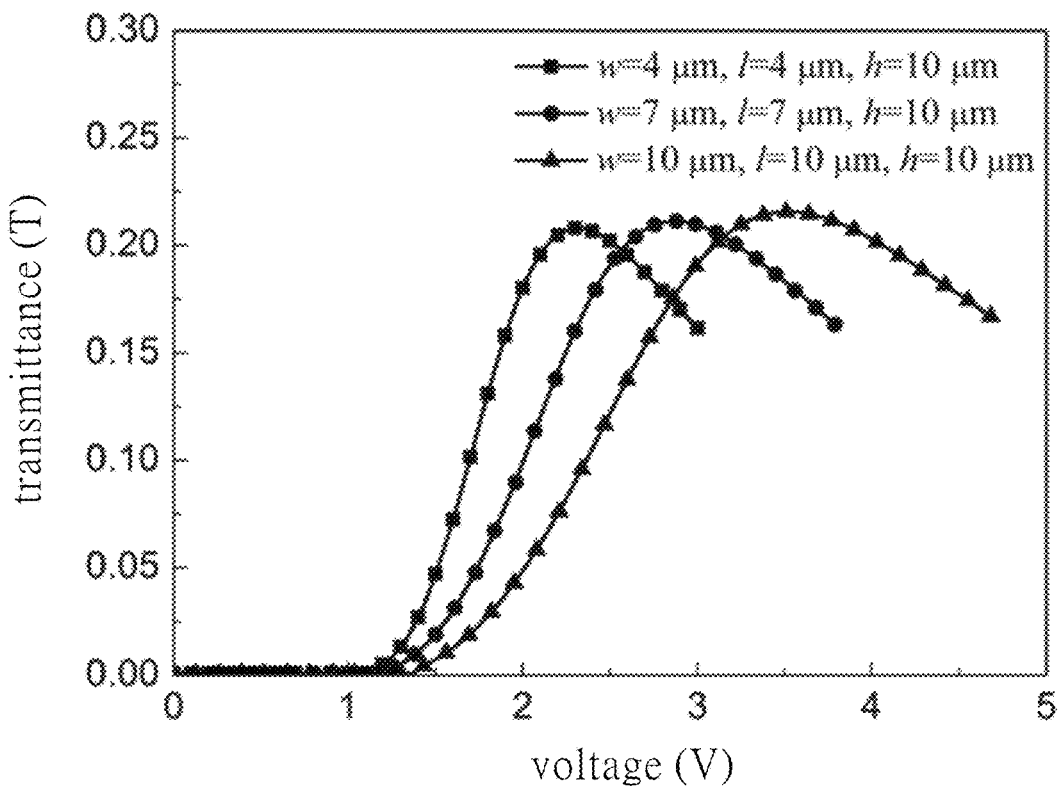
FIG. 6 is a voltage-transmittance graph of using a positive type liquid crystal as a liquid crystal layer in the third preferred embodiment of the invention.
Figure 7:
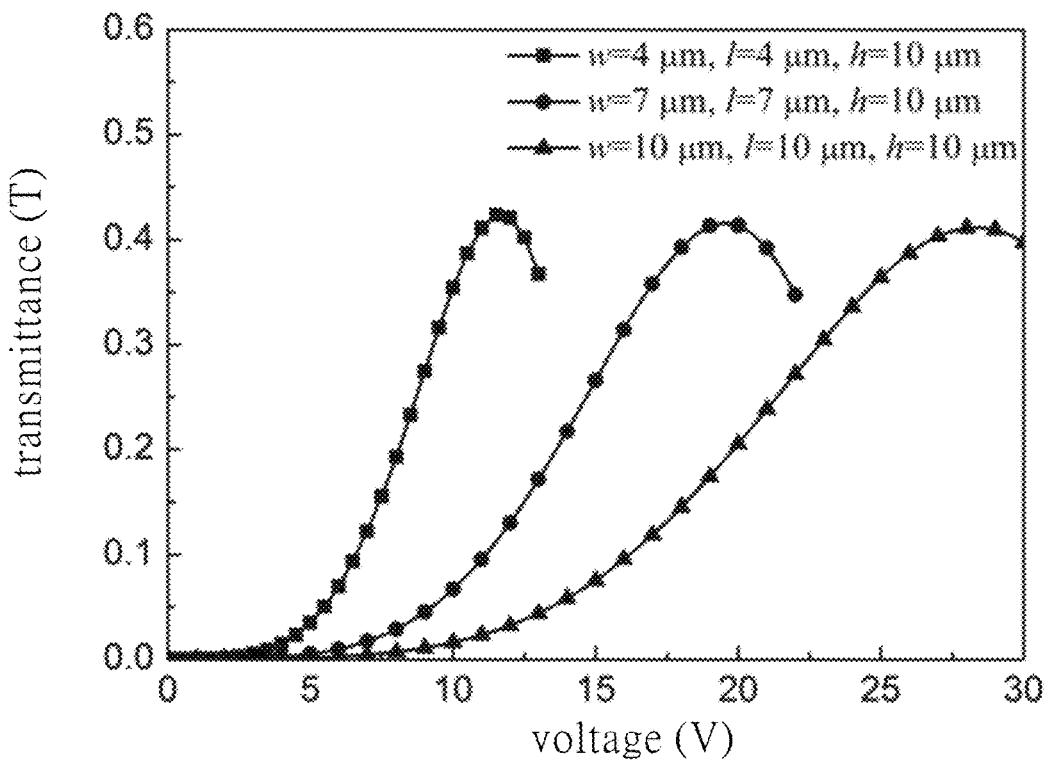
FIG. 7 is a voltage-transmittance graph of using a blue phase liquid crystal as a liquid crystal layer in the third preferred embodiment of the invention.

Further, when a material used for the liquid crystal layer 23 is blue phase liquid crystal, a voltage-transmittance graph is as shown in FIG. 7, where variables of the height h and the width t are fixed under conditions as shown in FIG. 6:

when both the width w and the interval l are 10 μm, driving voltage is 28.5V and transmittance is 0.41;
when both the width w and the interval l are 7 μm, driving voltage is 19.5V and transmittance is 0.41;
when both the width w and the interval l are 4 μm, driving voltage is 11.5V and transmittance is 0.42;
compared with the conventional blue-phase liquid crystal driving voltage as high as 35V to 40V, reduction effect that the third preferred embodiment is capable of achieving has reached a significant level.

Figure 8:
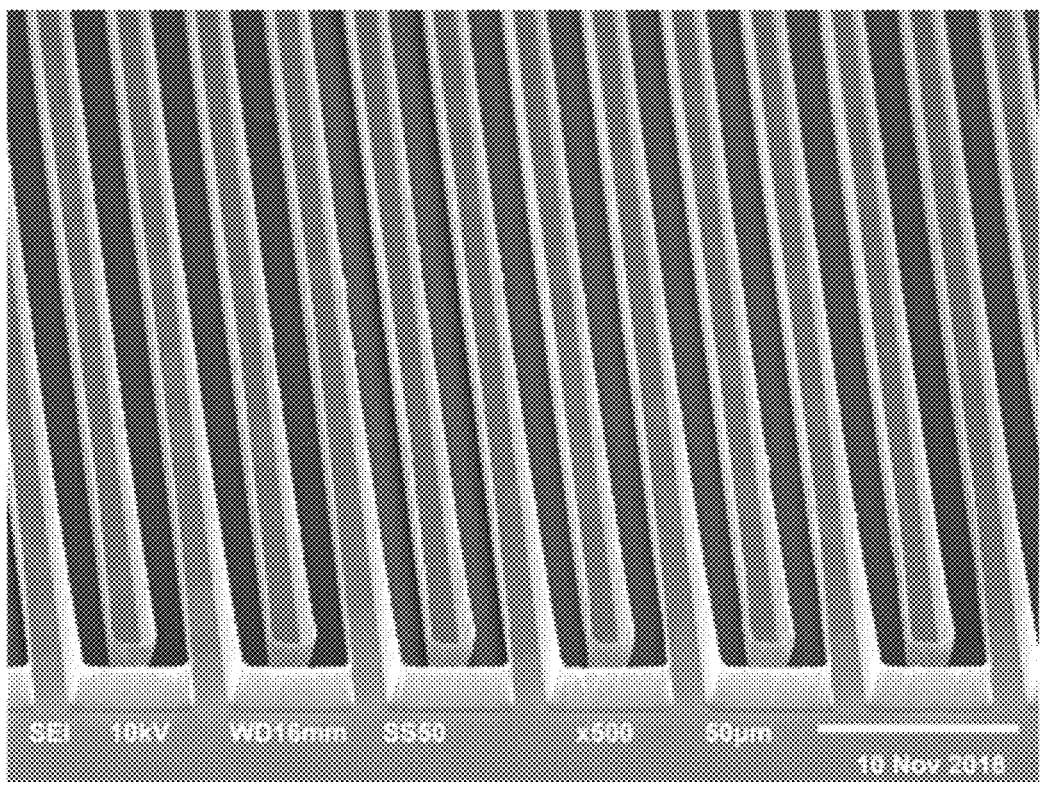
FIG. 8 is an actual image of the third preferred embodiment of the present invention, that is, an image taken with a scanning electron microscope from the first baseplate to the second baseplate and tilted at 45°.

In addition, FIG. 8 is an actual image of the third preferred embodiment.

Figure 9:
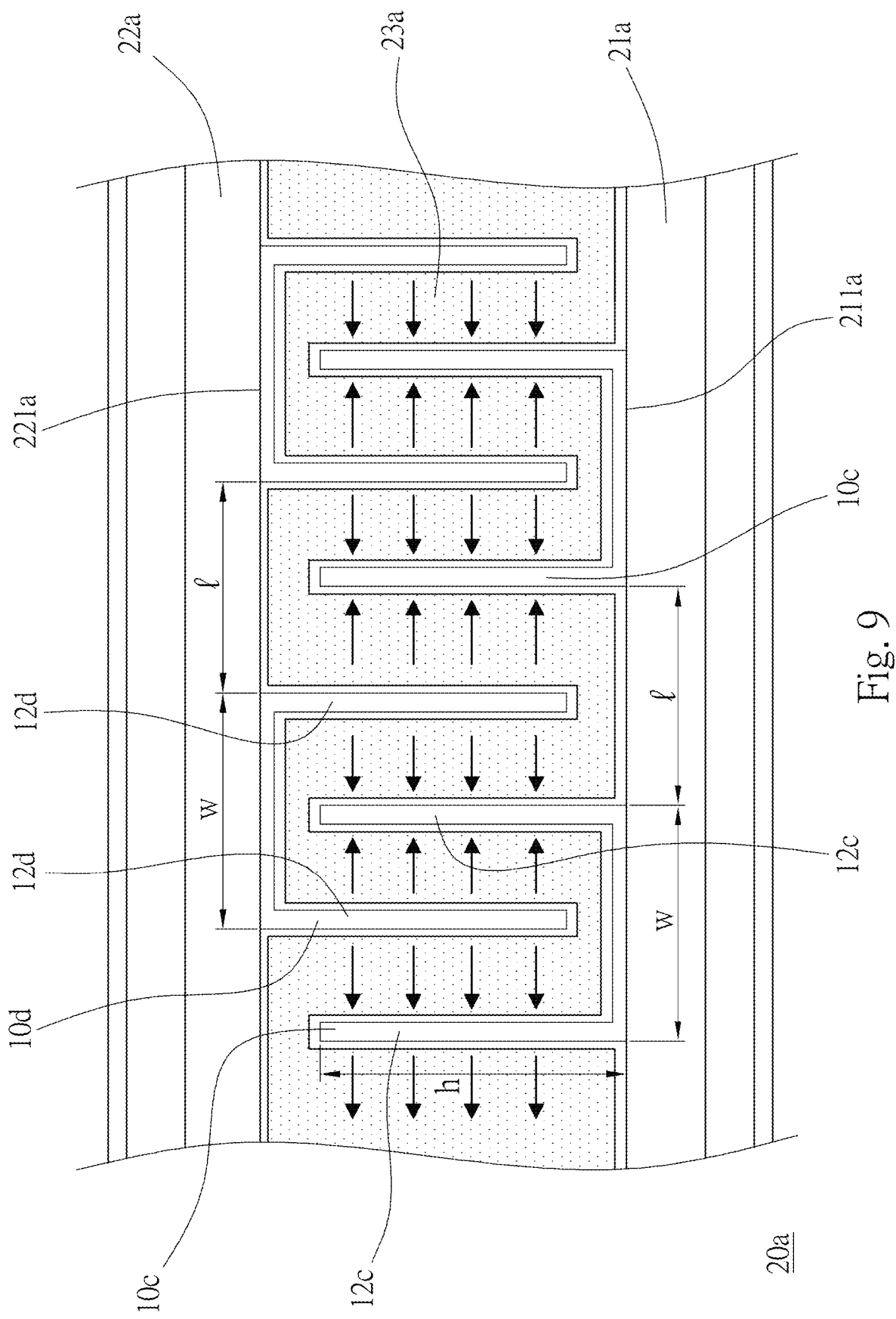
FIG. 9 is a partial plan view of a fourth preferred embodiment of the invention.
Figure 10:
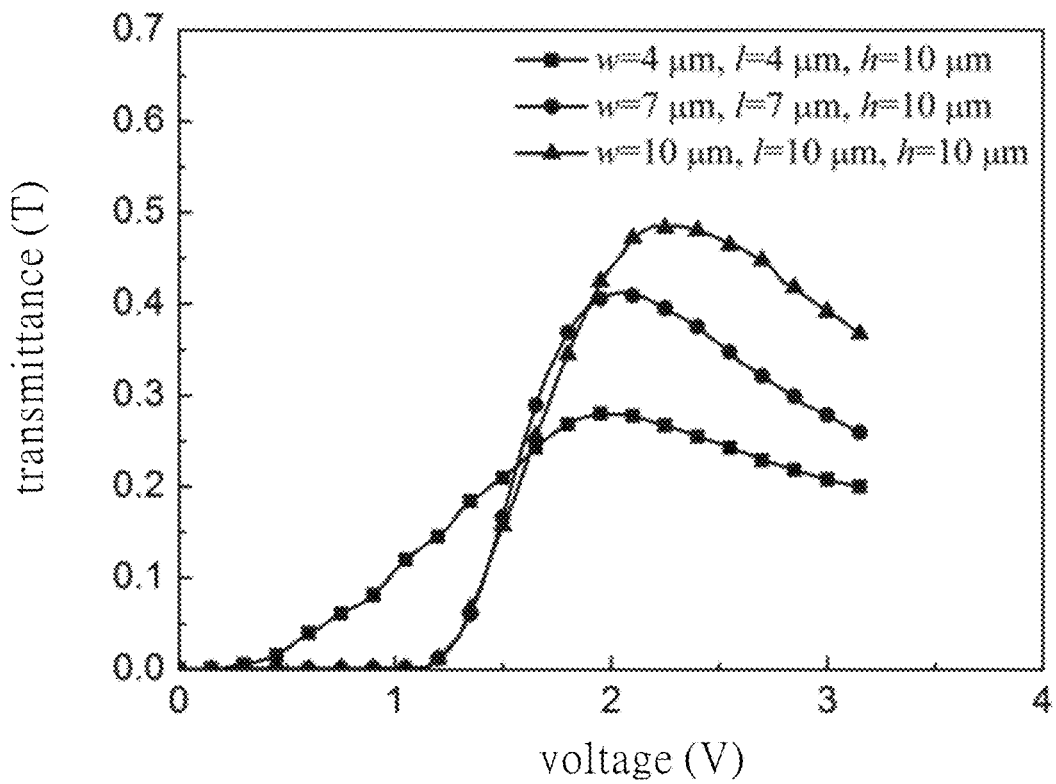
FIG. 10 is a voltage-transmittance graph of using a positive type liquid crystal as a liquid crystal layer in the fourth preferred embodiment of the invention.
Figure 11:
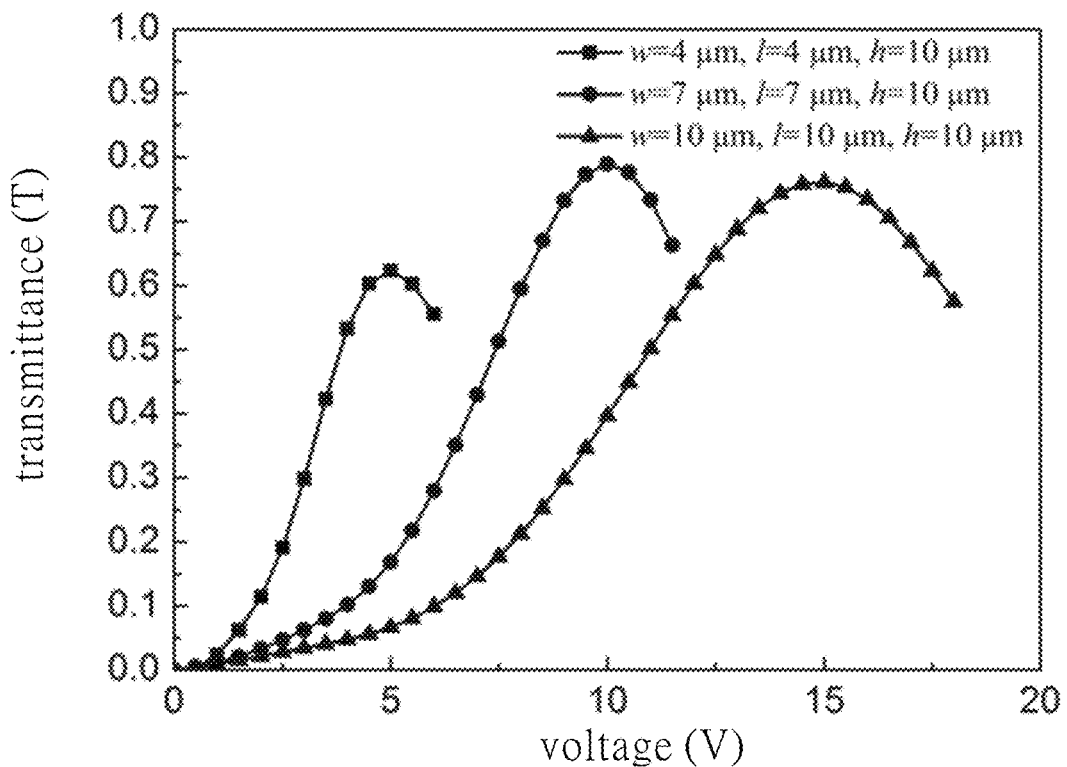
FIG. 11 is a voltage-transmittance graph of using a blue phase liquid crystal as a liquid crystal layer in the fourth preferred embodiment of the invention.

Please continue to refer to a fourth preferred embodiment of the invention shown in FIG. 9, where the electrode unit provided by the first preferred embodiment is used as common electrodes 10c and pixel electrodes 10d of a liquid crystal element 20a similar to the third preferred embodiment.

Wherein constitution of the liquid crystal element 20a is similar to that disclosed in the third preferred embodiment, and comprises a first baseplate 21a and a second baseplate 22a that are separated from each other, and a liquid crystal layer 23a sealed in a gap space of about 1 μm to 25 μm between the first baseplate 21a and the second baseplate 22a, wherein, when the liquid crystal layer 23a is positive type liquid crystal, a voltage-transmittance graph is as shown in FIG. 10, and when the liquid crystal layer 23a is blue phase liquid crystal, a voltage-transmittance graph is as shown in FIG. 11.

Each of the electrode units is respectively disposed on a side plane 211a of the first baseplate 21a facing the second baseplate 22a, and on a side plane 221a of the second baseplate 22a facing the first baseplate 21a. The electrode units disposed on the first baseplate 21a are respectively served as the common electrode 10c, and the electrode units disposed on the second baseplate 22a are respectively served as the pixel electrode 10d. Wherein the interval l spaced between the adjacent pixel electrodes 10d is the same as the interval l spaced between the adjacent common electrodes 10c, for each pair of the pixel electrode 10d and the common electrode 10c adjacent to each other, a side portion 12d of the pixel electrode 10d and a side portion 12c of the common electrode 10c are inserted into a U-shaped opening of each other in a staggered manner, so that the side portion 12d of each of the pixel electrodes 10d and the side portions 12c of each of the common electrodes 10c alternately correspond to each other sequentially.

The fourth preferred embodiment is capable of greatly increasing an intensity of the horizontal electric field E formed by an alternate spatial pattern of the side portions 12c, 12d, and compared with the technical content disclosed in the third preferred embodiment, a driving voltage of liquid crystal alignment can be further reduced, and a transmittance can also be further improved.

Please refer to FIG. 10, when a liquid crystal material used in the liquid crystal layer 23*a* in the fourth preferred embodiment is positive liquid crystal, and under conditions of the height h being set to 10 μm and the width t being set to 0.5 μm:

when the width w is 10 μm and the interval 1 is 10 μm, driving voltage is 2.20V and transmittance is 0.48;
when the width w is 7 μm and the interval 1 is 7 μm, driving voltage is 2.05V and transmittance is 0.41;
when the width w is 4 μm and the interval 1 is 4 μm, driving voltage is 1.95V and transmittance is 0.28;
obviously, it is indeed sufficient to further reduce a driving voltage compared to the third preferred embodiment.

Please refer to FIG. 11. When a liquid crystal material used in the liquid crystal layer 23*a* in the fourth preferred embodiment is blue phase liquid crystal material, and under conditions of the height h being set to 10 μm and the width t being set to 0.5 μm:

when the width w is 10 μm and the interval 1 is 10 μm, driving voltage is 15V and transmittance is 0.76;
when the width w is 7 μm and the interval 1 is 7 μm, driving voltage is 10V and transmittance is 0.78;
when the width w is 4 μm and the interval 1 is 4 μm, driving voltage is 5V and transmittance is 0.78;
these effects of significantly reducing a driving voltage of blue phase liquid crystal are sufficient to completely overcome the drawback of excessively high driving voltage of the conventional blue phase liquid crystal, so that the invention can be further widely applied in different industrial fields.

In summary, when the U-shaped coplanar electrode unit provided by the invention is applied to be used as an electrode element of a liquid crystal element, a significant degree of driving voltage reduction achieved has been confirmed to be capable of greatly increasing an intensity of horizontal electric field, using positive type liquid crystal as an example, within ranges of the previously disclosed embodiments, optimum parameters thereof are capable of obtaining a transmittance of 0.41 with a driving voltage of 1.95V; compared with the conventional FFS technology with a driving voltage of 4.1V only capable of achieving a transmittance of 0.24, the invention has achieved remarkable efficacies. In the alignment driving technology of blue phase liquid crystal, within ranges of the previously disclosed embodiments, optimum parameters thereof are capable of obtaining a transmittance of 0.63 with a driving voltage of only 5V; compared with the conventional technology with a driving voltage as high as 35V to be sufficient to drive blue phase liquid crystal for alignment, the invention is indeed capable of significantly reducing a driving voltage of blue phase liquid crystal, so that application of blue phase liquid crystal can be further expanded.

Herein, it is necessary to make a special explanation. Although applications of the third and fourth preferred embodiments in the first preferred embodiment is exemplified by liquid crystal display technology, the electrode unit disclosed in the first preferred embodiment is not limited to be only applied in liquid crystal display technology. In other words, the U-shaped coplanar electrode unit provided by the invention can be applied to be used not only as constitution of a liquid crystal element, but can also be used as an electrode for other objects, such as light-emitting element, solar cell element, driving element, control element, sensing element, detection element, capacitive element, mass transfer element, metamaterial element, thermoelectric element, heat dissipation element, optical element, or other functional components, it is not necessary to limit by usages or applications.

Figure 12:
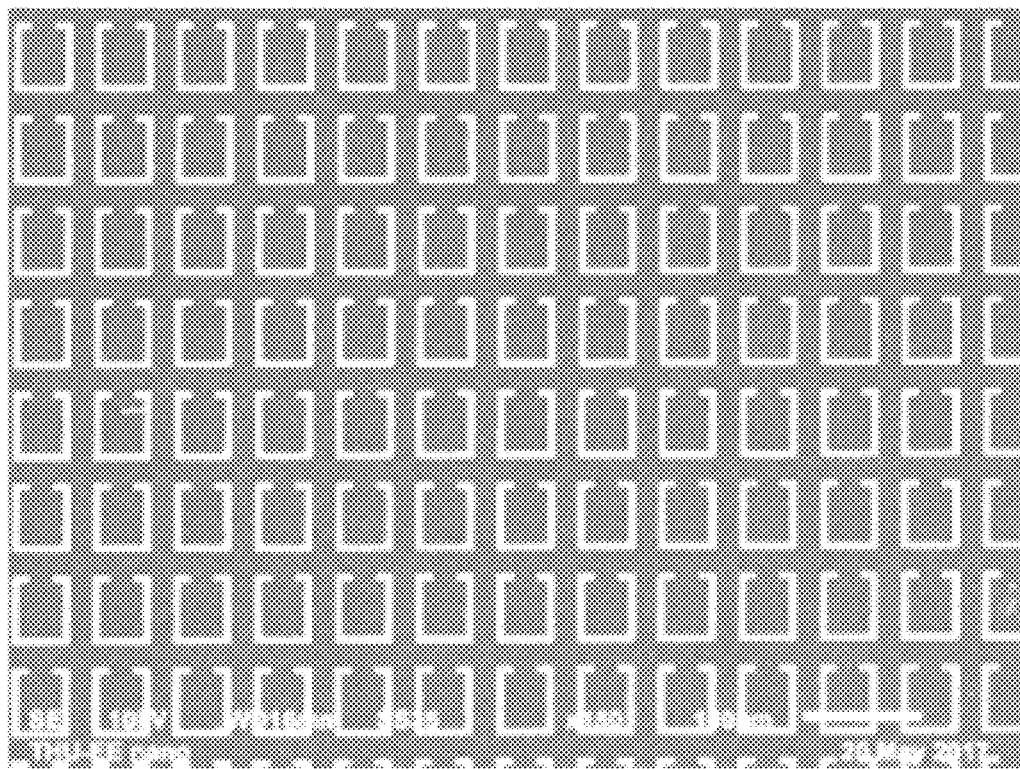
FIG. 12 is a schematic structural view of a traditional metamaterial element.
Figure 13:
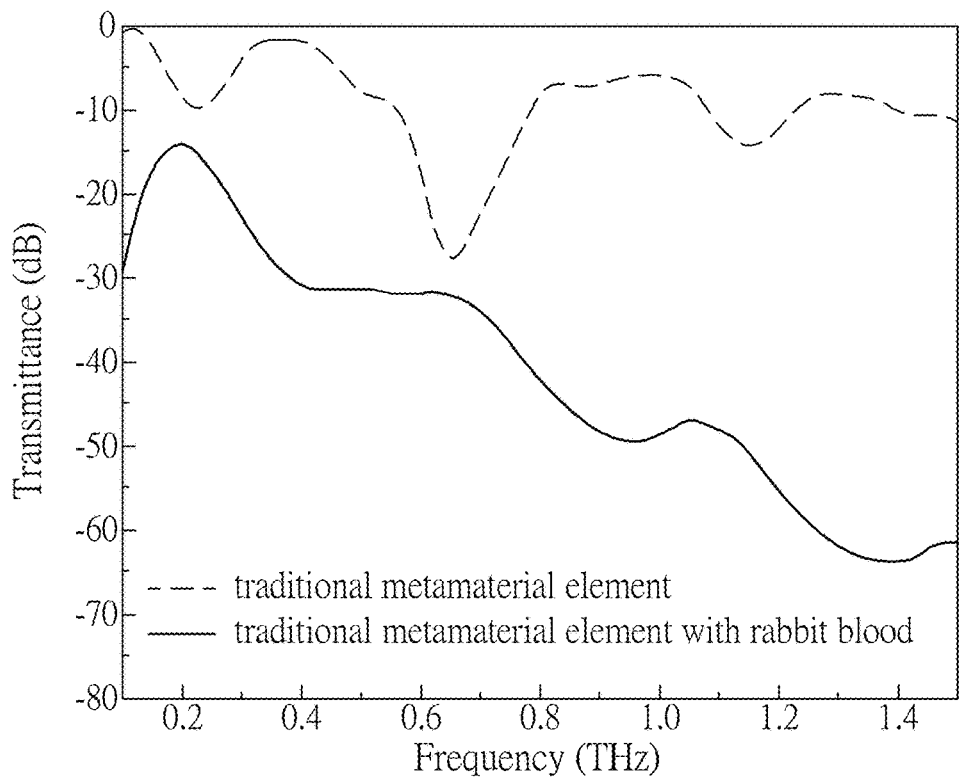
FIG. 13 is a spectrum diagram of the resonance signal of traditional metamaterials detecting rabbit blood.

Among them, taking the metamaterial element as an example, it can be used for high-sensitivity detection at megahertz frequency, and because the wavelength of the megahertz wave is very long, the detection can be proceeded without destroying the sample. Moreover, the photon energy of the megahertz wave is low, which is a relatively safe wave band compared with X-rays. Therefore, the megahertz wave has great advantages in biomedical applications. However, traditional metamaterial element is a planar two-dimensional structure composed of periodic metallic split-ring resonators (SRRs), as shown in FIG. 12, it cannot detect samples containing water. The reason is that the megahertz wave absorbs water so much that there is no signal during detection, and so it is difficult to apply it in biomedicine, such as detecting blood. As shown in FIG. 13, it is a resonance signal spectrum diagram of rabbit blood with a thickness of 188 um on a traditional metamaterial element. Among them, the dotted line is the resonance spectrum curve of the traditional metamaterial element, its resonance frequency is 0.654 THz, and the resonance intensity is 25 dB, while the solid line is the resonance spectrum curve of the traditional metamaterial element with rabbit blood, but there is no resonance signal.

Figure 14:
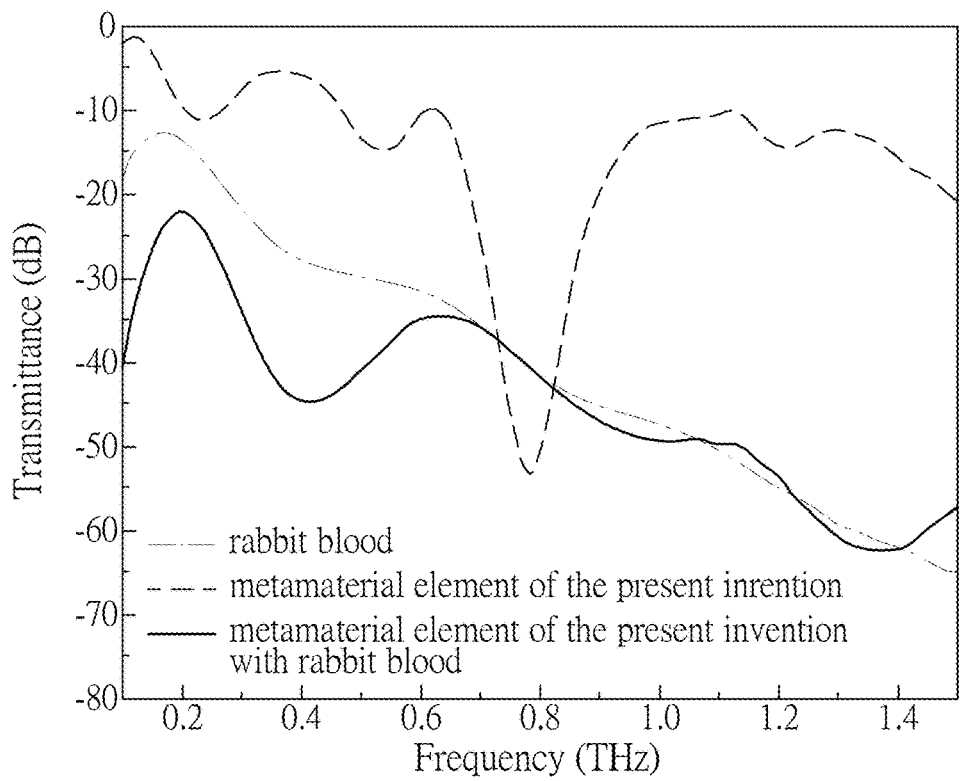
FIG. 14 is a spectrum diagram of the resonance signal of the present invention applied to the metamaterial to detect rabbit blood.
Figure 15:
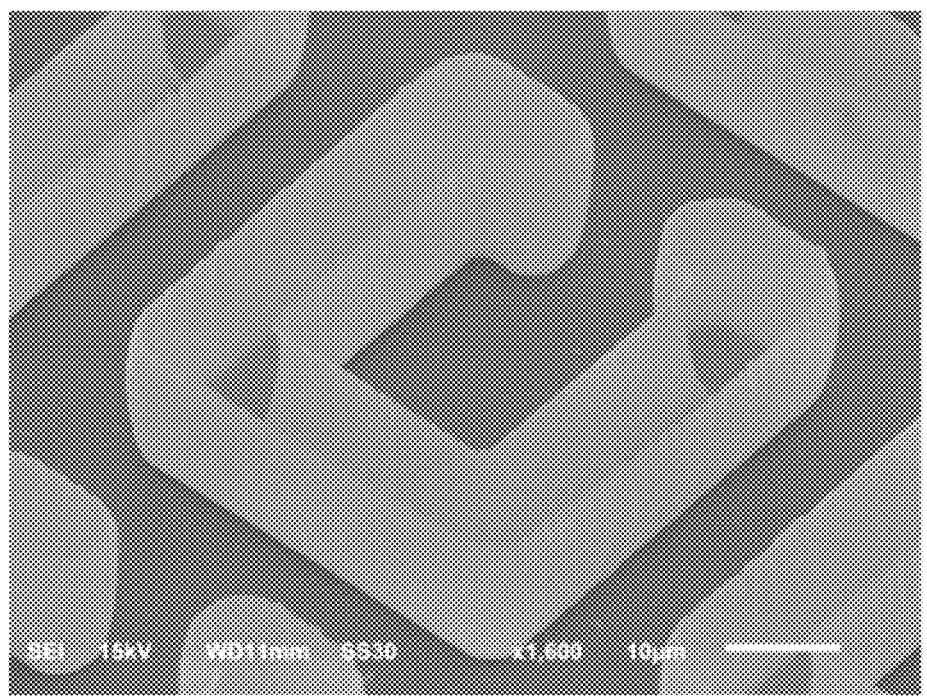
FIG. 15 is a schematic diagram of the structure disclosed in FIG. 14, that is, an image of the U-shaped structure of the metamaterial element taken by a scanning electron microscope.

After that, FIG. 14 is the resonance signal spectrum diagram of the present invention as an electrode of a metamaterial element and used to detect rabbit blood, wherein, the dotted line is the resonance spectrum curve of the metamaterial element of the present invention, its resonance frequency is 0.776 THz, and the resonance intensity is 53 dB. The resonance frequency of the metamaterial element of the present invention is greater than that of the traditional metamaterial element, because the metal wall of the U-shaped structure of the metamaterial element of the present invention can increase its surface electric current, as shown in FIG. 15, enhancing the resonance signal. A dot-chain line is the resonance spectrum curve of rabbit blood with a thickness of 188 um, which indicates that the blood absorbs most of the megahertz waves. The solid line is the resonance spectrum curve of the metamaterial element of the present invention loaded with rabbit blood with a thickness of 188 um, its resonance frequency is from 0.776 THz redshift to 0.420 THz, and the resonance intensity is 40.1 dB. The reason for the red shift is that metamaterials are more sensitive to changes in the refractive index, that is, the surrounding medium changes from air to rabbit blood, and the refractive index of rabbit blood is higher than that of air, resulting in red shift. Moreover, its resonance intensity becomes stronger, and so the resonance signal of rabbit blood can be detected, which cannot be detected by traditional metamaterial elements. Therefore, the metamaterial element of the present invention can be applied to biosensors.

Figure 16:
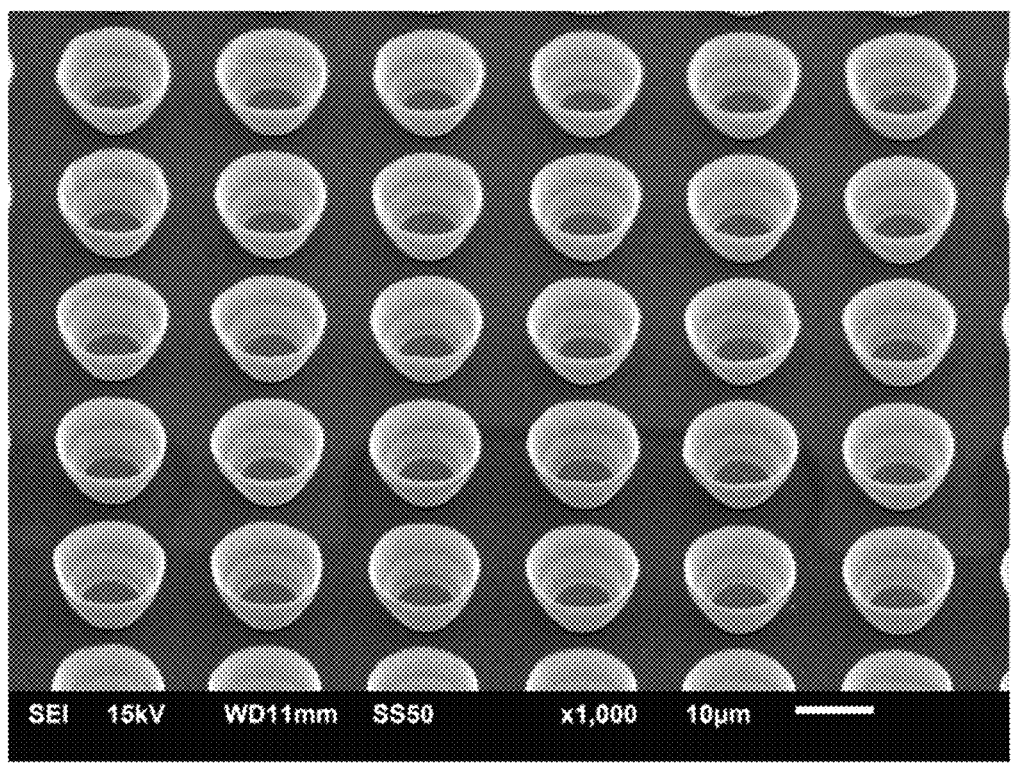
FIG. 16 is an image taken by a scanning electron microscope of the U-shaped coplanar electrode unit of the present invention disposed on a metal plate.
Figure 17:
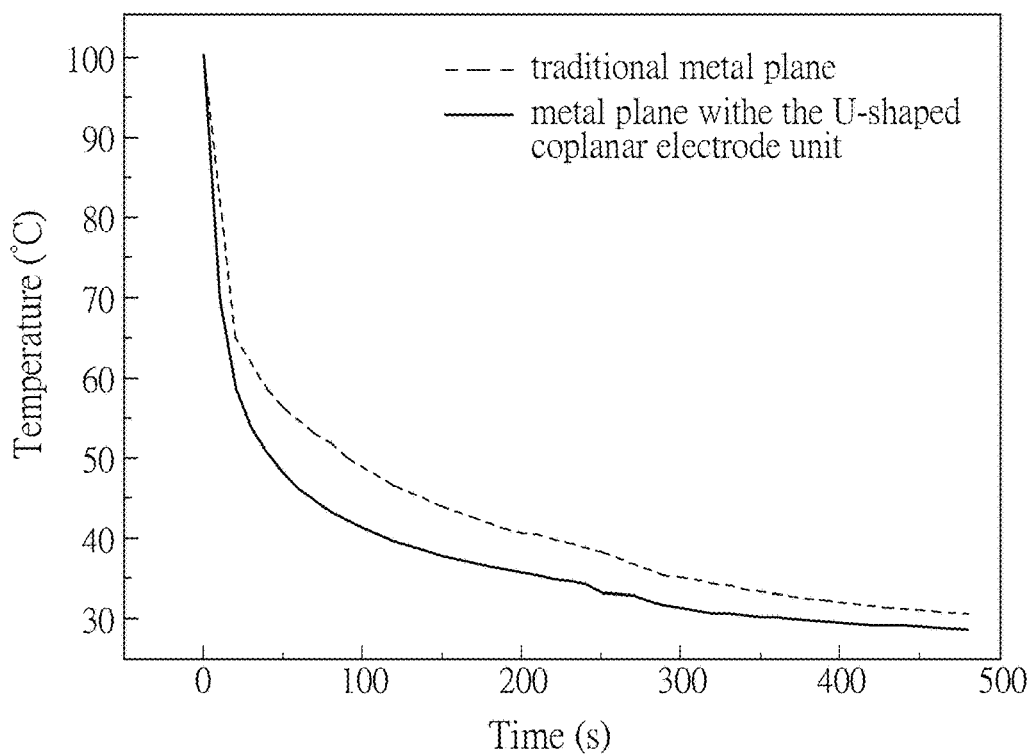

Furthermore, a shape of the U-shaped unit provided by the invention is not limited to those disclosed in the above embodiments. For example, when each of the side portions extends outward from the two sides of the base in a same direction, each of the side portions further extends laterally and connects to each other in a ring shape, so that after each of the side portions extends, a cross-section formed together with the base is in a cylindrical U-shape. It can also be applied to heat dissipation components to greatly improve the heat dissipation effect. Specifically, as shown in FIG. 16, multiple sets of U-shaped coplanar electrode units are disposed on the metal plate, and the size is 7 um. The heat dissipation efficiency diagram of the actual test shown in FIG. 17 compares the heat dissipation performance of the traditional metal plate and the metal plate with the U-shaped coplanar electrode unit disposed on, and its measurement time is 8 minutes, and a data is recorded every 10 seconds. The dotted line in the figure is the heat dissipation curve of the traditional metal plate, and the solid line is the heat dissipation curve of the metal plate with the U-shaped coplanar electrode unit disposed on.

In addition, the base can further comprise two base bodies, and each of the side portions extends outward in a same direction from one end of each of the base bodies opposite to each other, so that in the U-shape commonly formed by each of the side portions and the base, the U-shaped closed end formed by the base is commonly formed by the separated base bodies, so that the U-shape is a discontinuous shape with the closed end being disconnected.

Figure 18:
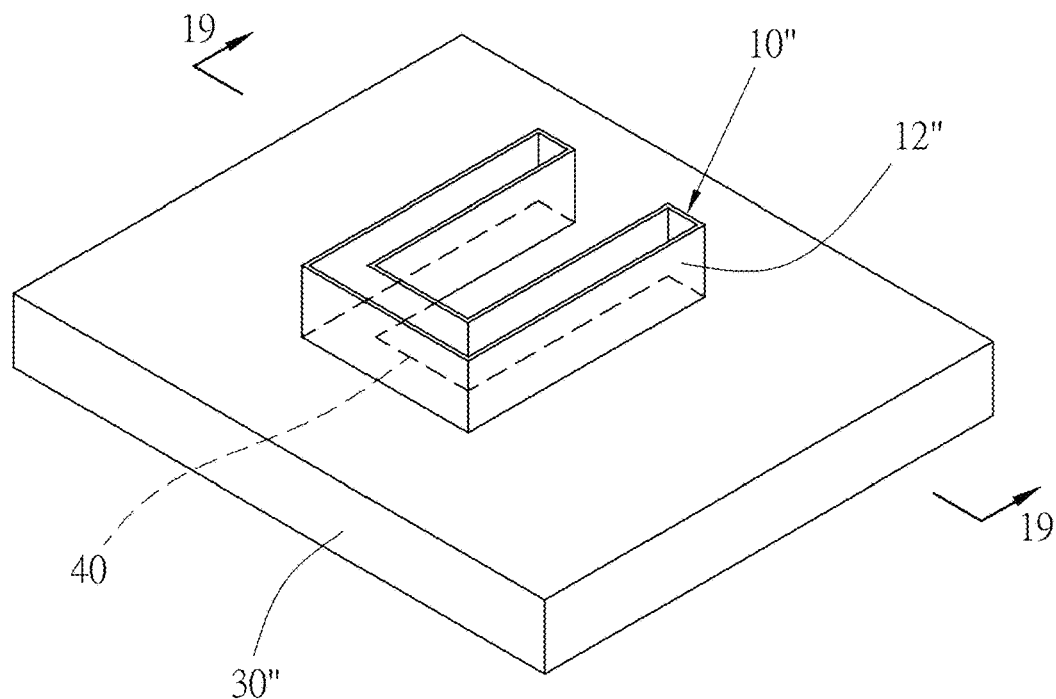
FIG. 18 is a schematic diagram of U-shaped units of the present invention disposed on conventional electrodes.
Figure 19:
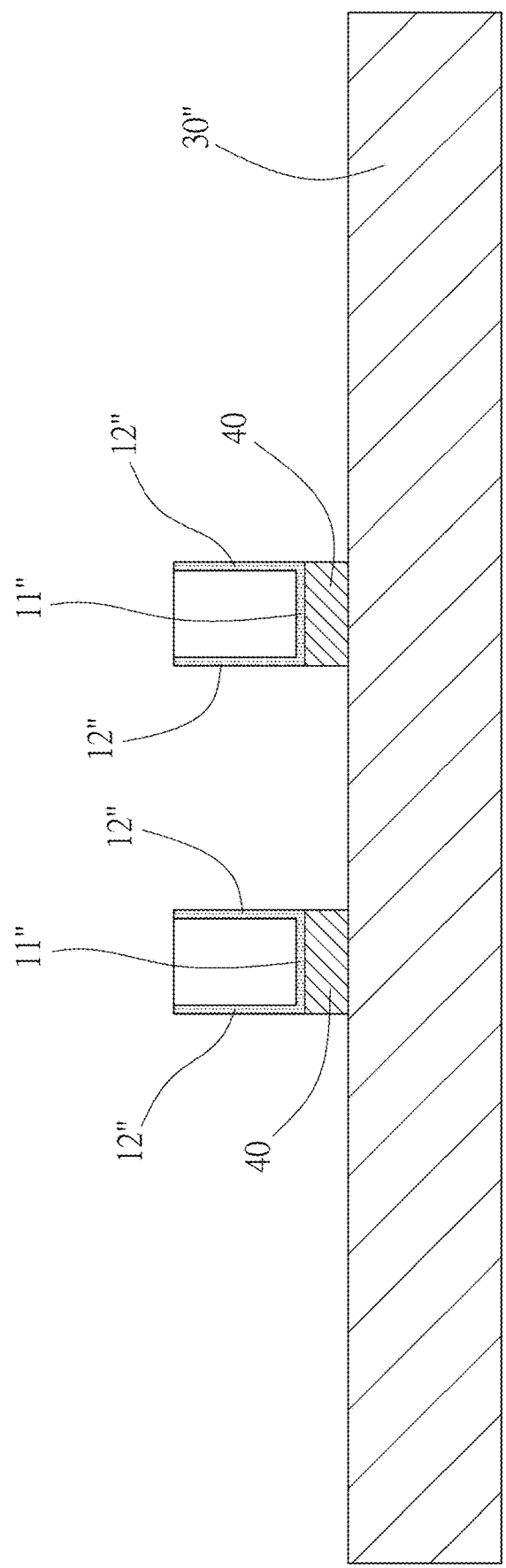
FIG. 19 is a sectional view along section line 19-19 of FIG. 18.

In addition, as shown in FIG. 18, the U-shaped unit (10") of the present invention is further disposed on the baseplate (30"), and use the base (11") as the bottom, being arranged on the surface of the conventional electrode (40) in accordance with the shape of the conventional electrode (40). Then, each side portions (12") is used as a wall, and the outer contour of the conventional electrode (40) extends away from the conventional electrode (40), so that its cross-section still presents a U-shape, as shown in the FIG. 19. Wherein, the shape of the traditional electrode (40) can be, but not limited to, C-shape, U-shape, circle, rectangle, parallelogram, polygon, rhombus, ellipse, or any variation based on the aforementioned shapes, and the conventional electrode (40) in this example is U-shaped. It is to be understood that the above description is only preferred embodiments of the present invention and is not used to limit the present invention, and changes in accordance with the concepts of the present invention may be made without departing from the spirit of the present invention, for example, the equivalent effects produced by various transformations, variations, modifications and applications made to the configurations or arrangements shall still fall within the scope covered by the appended claims of the present invention.

What is claimed is:

1. A U-shaped unit, which is molded on a baseplate, and the U-shaped unit includes:
   a base portion located on a first side plate surface of the baseplate, and extending a predetermined width along a virtual first axis parallel to the plane of the first side plate surface; and
   two side portions, each side portion of the two side portions has a first end and a second end, the first end of each said side portion of the two side portions is respectively fixed to one of the two ends of the base portion in the first axis direction, and the second end of each side portion of the two side portions respectively extends outwardly away from the base portion and is spaced apart and not directly connected to an adjacent U-shaped section, and each side portion of the two side portions respectively extends along a second axis direction separated from the first axis direction by a predetermined angle and not on the same plane as the first axis, and the two side portions jointly form a U-shaped section with the base, and the ratio of the individual width of each side portions in the direction of the first axis to the individual height in the direction of the second axis is between 1:20 and 1:2.

2. The U-shaped unit as claimed in claim 1, wherein an included angle between the first axis and the second axis is between 45 degrees and 135 degrees.

3. The U-shaped unit as claimed in claim 1, being made of transparent conductive material, metal material, dielectric material or semiconductor material.

4. The U-shaped unit as claimed in claim 1, wherein the base further comprises two separated base bodies, and each of the side portions respectively extends outward in a same direction from one end of each of the base bodies opposite to each other, thereby each of the base bodies causes the formed U-shape being a discontinuous shape.

5. The U-shaped unit as claimed in claim 1, wherein each of the side portions connects to each other in a ring shape.

6. The U-shaped unit as claimed in claim 1, being a unit of a biosensing element, a unit of an electrode element, a unit of a heat dissipation element, or a unit of an optical element.

7. A liquid crystal element with U-shaped coplanar electrode units comprising:
   a first baseplate;
   a second baseplate separated from the first baseplate; and
   a liquid crystal layer sealed between the first baseplate and the second baseplate;
   each U-shaped coplanar electrode unit of the U-shaped coplanar electrode units being respectively the U-shaped unit served as the electrode unit as claimed in claim 1, and being located on one side of the first baseplate facing the second baseplate, each of the side portions extending into the liquid crystal layer, and making a height of each of the side portions greater than half of a distance between the first baseplate and the second baseplate.

8. The liquid crystal element with the U-shaped coplanar electrode units as claimed in claim 7, wherein adjacent U-shaped coplanar electrode units are separated from each other by a distance between 3 nm and 20 μm.

9. The liquid crystal element with the U-shaped coplanar electrode units as claimed in claim 7, wherein each of the U-shaped coplanar electrode units is further provided on one side of the second baseplate facing the first baseplate, and each of the U-shaped coplanar electrode units located on the first baseplate and each of the U-shaped coplanar electrode units located on the second baseplate face each other with a U-shaped opening portion, and the single side portion of each of the U-shaped coplanar electrode units on the first baseplate and the single side portion of each of the U-shaped coplanar electrode units on the second baseplate are inserted into the U-shaped opening of each other.

10. The liquid crystal element with the U-shaped coplanar electrode units as claimed in claim 9, wherein an interval between adjacent U-shaped coplanar electrode units located on the first baseplate is equal to an interval between adjacent U-shaped coplanar electrode units located on the second baseplate.

11. The U-shaped unit as claimed in claim 1, wherein, when a first U-shaped unit is located adjacent to a second U-shaped unit, the second ends of the two side portions of the first U-shaped unit are space apart and not directly connected to the second ends of the two side portions of the second U-shaped unit.

* * * * *